(12) United States Patent
Zhang et al.

(10) Patent No.: US 10,369,407 B2
(45) Date of Patent: Aug. 6, 2019

(54) FITNESS EQUIPMENT AND AUTOMATIC OXYGEN-GENERATING FITNESS EQUIPMENT

(71) Applicant: SHENZHEN GOOD FAMILY ENTERPRISE CO., LTD., Shenzhen, Guangdong Province (CN)

(72) Inventors: Jiaxing Zhang, Shenzhen (CN); Liwei Lu, Shenzhen (CN); Senping Liu, Shenzhen (CN)

(73) Assignee: SHENZHEN GOOD FAMILY ENTERPRISE CO., LTD., Shenzhen, Guangdong Province (CN)

( * ) Notice: Subject to any disclaimer, the term of this patent is extended or adjusted under 35 U.S.C. 154(b) by 1019 days.

(21) Appl. No.: 14/833,050

(22) Filed: Aug. 22, 2015

(65) Prior Publication Data

US 2016/0051847 A1 Feb. 25, 2016

(30) Foreign Application Priority Data

Aug. 22, 2014 (CN) .................... 2014 2 0478442 U
Aug. 3, 2015 (CN) ......................... 2015 1 0478960

(51) Int. Cl.
*F03G 5/00* (2006.01)
*F03G 5/06* (2006.01)
(Continued)

(52) U.S. Cl.
CPC ....... *A63B 23/0476* (2013.01); *A61M 16/101* (2014.02); *A61M 16/16* (2013.01);
(Continued)

(58) Field of Classification Search
CPC ............ A63B 23/0476; A63B 22/0605; A63B 24/0087; A61M 16/101; A61M 16/16;
(Continued)

(56) References Cited

U.S. PATENT DOCUMENTS 3,657,517 A * 4/1972 Hoyt ..................... A61M 5/445
219/439
3,776,215 A * 12/1973 Howard .................... F24F 6/14
126/113

(Continued)

FOREIGN PATENT DOCUMENTS

CN 2241550 Y 12/1996
CN 201199115 Y * 2/2009
(Continued)

*Primary Examiner* — Gregory A Anderson
*Assistant Examiner* — Brian M. Booker
(74) *Attorney, Agent, or Firm* — Cheng-Ju Chiang

(57) ABSTRACT

A fitness equipment and an automatic oxygen-generating fitness equipment are disclosed. The fitness equipment comprises a power unit, a sensor unit and an oxygen-generating assembly. The power unit comprises a belt drive turnplate, a belt and a magnetic wheel. Rotation of the belt drive turnplate drives the belt to operate so that the magnetic wheel is driven to rotate. The sensor unit is adapted to detect the belt drive turnplate and generate an activation signal when the belt drive turnplate is rotating. The oxygen-generating assembly comprises a control unit, a motor and an oxygen generator. The control unit is configured to receive the activation signal from the sensor so that the motor is activated to drive the oxygen generator to operate. The control unit may also control the equipment to switch between an oxygen-generating mode and a non-oxygen-generating mode.

19 Claims, 8 Drawing Sheets

(51) Int. Cl.
*A61M 16/16* (2006.01)
*A63B 21/22* (2006.01)
*A63B 22/06* (2006.01)
*A63B 23/04* (2006.01)
*A63B 24/00* (2006.01)
*C01B 13/02* (2006.01)
*A63B 21/005* (2006.01)
*A61M 16/10* (2006.01)
*B01D 53/04* (2006.01)
*A62B 19/00* (2006.01)
*B01D 53/02* (2006.01)

(52) U.S. Cl.
CPC ...... *A63B 22/0605* (2013.01); *A63B 24/0087* (2013.01); *B01D 53/04* (2013.01); *C01B 13/0281* (2013.01); *C01B 13/0296* (2013.01); *F03G 5/00* (2013.01); *F03G 5/06* (2013.01); *A61M 16/162* (2013.01); *A61M 2202/0208* (2013.01); *A61M 2205/3365* (2013.01); *A61M 2205/825* (2013.01); *A61M 2205/8206* (2013.01); *A61M 2205/8256* (2013.01); *A62B 19/00* (2013.01); *A63B 21/0051* (2013.01); *A63B 21/0053* (2013.01); *A63B 21/225* (2013.01); *A63B 2022/0611* (2013.01); *A63B 2024/0093* (2013.01); *A63B 2213/005* (2013.01); *A63B 2220/24* (2013.01); *A63B 2220/34* (2013.01); *A63B 2220/44* (2013.01); *A63B 2220/58* (2013.01); *B01D 53/02* (2013.01); *B01D 2253/102* (2013.01); *B01D 2253/116* (2013.01); *B01D 2256/12* (2013.01); *B01D 2257/102* (2013.01); *B01D 2258/06* (2013.01); *B01D 2259/45* (2013.01)

(58) Field of Classification Search
CPC ........ A61M 16/162; A61M 2202/0208; A61M 2205/3365; A61M 2205/8206; A61M 2205/825; B01D 53/04; C01B 13/0281; C01B 13/0296; F03G 5/00; F03G 5/06
USPC .............................................. 482/50–52, 57
See application file for complete search history.

(56) References Cited

U.S. PATENT DOCUMENTS

| | | | | |
|---|---|---|---|---|
| 3,982,751 A * | 9/1976 | Obenshain | ............ | B65H 31/38 271/221 |
| 4,154,234 A * | 5/1979 | Baker | ............ | A62B 7/08 128/205.12 |
| 4,362,153 A * | 12/1982 | Wilson | ............ | A62B 7/10 128/202.26 |
| 4,723,786 A * | 2/1988 | Buchanan | ............ | B62K 19/34 280/259 |
| 5,665,036 A * | 9/1997 | Hsieh | ............ | A63B 23/00 482/100 |
| 6,004,243 A * | 12/1999 | Ewert | ............ | A63B 24/00 386/E5.002 |
| 6,027,429 A * | 2/2000 | Daniels | ............ | A63B 21/0056 482/111 |
| 6,267,114 B1 * | 7/2001 | Ueno | ............ | A62B 21/00 128/200.24 |
| 6,358,189 B1 * | 3/2002 | Koenig | ............ | A63B 21/0615 482/136 |
| 6,504,259 B1 * | 1/2003 | Kuroda | ............ | B60K 6/46 290/40 C |
| 6,666,799 B2 * | 12/2003 | Hildebrandt | ............ | A63B 21/157 482/57 |
| 6,672,998 B2 * | 1/2004 | Cook | ............ | A63B 21/00181 482/142 |
| 6,752,748 B1 * | 6/2004 | Scotti | ............ | A63B 21/0615 482/140 |
| 7,452,310 B2 * | 11/2008 | Wang | ............ | A63B 22/02 128/202.12 |
| 7,736,281 B2 * | 6/2010 | Corbalis | ............ | A63B 22/0605 248/444.1 |
| 7,833,143 B1 * | 11/2010 | Tsai | ............ | A63B 21/0552 482/140 |
| 8,007,412 B2 * | 8/2011 | Lofgren | ............ | A63B 22/0002 482/62 |
| 8,371,992 B2 * | 2/2013 | Irving | ............ | A63B 21/015 482/57 |
| 8,485,945 B2 * | 7/2013 | Leonhard | ............ | A63B 21/0052 482/52 |
| 9,126,076 B2 * | 9/2015 | Liang | ............ | A63B 21/0053 |
| 9,272,185 B2 * | 3/2016 | Dugan | ............ | A63B 24/00 |
| 9,764,178 B1 * | 9/2017 | Wein | ............ | A63B 21/0055 |
| 9,839,808 B1 * | 12/2017 | McNeil | ............ | A63B 23/18 |
| 9,901,780 B2 * | 2/2018 | DeLuca | ............ | A63B 24/0087 |
| 9,937,382 B2 * | 4/2018 | Dugan | ............ | A63B 24/00 |
| 2002/0070559 A1 * | 6/2002 | Chen | ............ | A63B 21/0053 290/50 |
| 2002/0147079 A1 * | 10/2002 | Kalnbach | ............ | A63B 21/0053 482/57 |
| 2003/0074985 A1 * | 4/2003 | Liao | ............ | B62J 99/00 73/862.195 |
| 2004/0009848 A1 * | 1/2004 | Lee | ............ | A63B 22/0605 482/57 |
| 2007/0023041 A1 * | 2/2007 | Wang | ............ | A63B 22/02 128/203.13 |
| 2008/0039293 A1 * | 2/2008 | Steinmetz | ............ | A63B 21/4047 482/100 |
| 2010/0317494 A1 * | 12/2010 | Wang | ............ | A63B 21/00181 482/110 |
| 2011/0266082 A1 * | 11/2011 | Yang | ............ | B60L 11/007 180/206.5 |
| 2012/0202649 A1 * | 8/2012 | Huber | ............ | A63B 69/16 482/2 |
| 2013/0005545 A1 * | 1/2013 | Wang | ............ | A61H 1/0244 482/142 |
| 2014/0014098 A1 * | 1/2014 | Elliott | ............ | A62B 7/08 128/201.23 |
| 2015/0290490 A1 * | 10/2015 | Badarneh | ............ | A63B 22/0023 482/6 |
| 2017/0001065 A1 * | 1/2017 | Irving | ............ | A63B 21/225 |
| 2017/0304669 A1 * | 10/2017 | LaCaze | ............ | A63B 21/169 |
| 2018/0078752 A1 * | 3/2018 | Gulliver | ............ | A61M 16/0666 |

FOREIGN PATENT DOCUMENTS

| | | | | |
|---|---|---|---|---|
| CN | 202777687 U | 3/2013 | | |
| CN | 203079685 U | 7/2013 | | |
| CN | 204182074 U | 3/2015 | | |
| CN | 105056477 A | 11/2015 | | |
| JP | H02-263704 A | 10/1990 | | |
| JP | 2003-265645 A | 9/2003 | | |
| WO | WO 2007109896 A1 * | 10/2007 | ............ | B65G 43/02 |
| WO | WO 2014084742 A1 * | 6/2014 | ......... | A63B 22/0023 |

* cited by examiner

FITNESS EQUIPMENT AND AUTOMATIC OXYGEN-GENERATING FITNESS EQUIPMENT

FIELD OF THE INVENTION

The present disclosure generally relates to the technical field of fitness facilities, and more particularly, to a fitness equipment and an automatic oxygen-generating fitness equipment.

BACKGROUND OF THE INVENTION

With improvement of people's living standards, there are more and more concerns about the health. Currently, various fitness equipments have become available on the market, e.g., dumbbells, hand-muscle developers, treadmills, exercise bicycles and so on. Most people exercise just on such fitness equipment.

However, the "exercises" alone cannot deliver the best effect because the exercisers need an additional amount of oxygen during strenuous exercises. Particularly for those who suffer from some respiratory diseases, a supply of oxygen must be ensured.

Currently, however, most of the fitness equipments are not provided with an oxygen supplying device.

SUMMARY OF THE INVENTION

The present disclosure provides a fitness equipment and an automatic oxygen-generating fitness equipment, which are mainly intended to solve the technical problem that the oxygen supply cannot be ensured for exercisers during strenuous exercises in the prior art.

To solve the aforesaid technical problems, a technical solution adopted by the present disclosure is to provide an automatic oxygen-generating fitness equipment, comprising a power unit, a sensor unit and an oxygen-generating assembly, wherein the power unit comprises a belt drive turnplate, a belt and a magnetic wheel, and rotation of the belt drive turnplate drives the belt to operate so that the magnetic wheel is driven to rotate; the sensor unit is adapted to detect the belt drive turnplate and generate an activation signal when the belt drive turnplate is rotating; and the oxygen-generating assembly comprises a control unit, a motor and an oxygen generator, and the control unit is configured to receive the activation signal so that the motor is activated to drive the oxygen generator to operate.

Wherein, the oxygen generator comprises a vacuum pump and an oxygen-rich film, and rotation of the motor drives the vacuum pump to generate an air stream so that air at a rated oxygen concentration is formed by the oxygen-rich film.

Wherein, the oxygen generator further comprises an oxygen bag, and the air at the rated oxygen concentration flows to the oxygen bag via the vacuum pump.

Wherein, the oxygen bag forms the air at the rated oxygen concentration into an air flow of 10 L/min for supply to an exerciser.

Wherein, the oxygen generator further comprises medical-grade silicone tubes, and the oxygen-rich film and the oxygen bag are connected to the vacuum pump via the medical-grade silicone tubes respectively.

Wherein, the rated oxygen concentration is 21%~30%.

Wherein, the power unit further comprises an electromagnet which is adapted to adjust rotation resistance of the magnetic wheel under the control of the control unit.

Wherein, the oxygen-generating assembly further comprises an external electric power source which supplies electric power to the motor via the control unit.

Wherein, the automatic oxygen-generating fitness equipment further comprises an armrest, a frame and a seat cushion support, wherein the power unit and the oxygen-generating assembly are disposed in the frame; the seat cushion support and the armrest are connected with the frame respectively, and the oxygen bag is disposed between the seat cushion support and the armrest to provide the exerciser with the air at the rated oxygen concentration.

Wherein, the power unit further comprises a crank and a pedal, wherein the crank is hinged to the belt drive turnplate; and the pedal is hinged to the crank and is adapted to drive the belt drive turnplate to rotate via the crank.

To solve the aforesaid technical problems, a technical solution adopted by the present disclosure is to provide a fitness equipment, comprising a support, a power unit, an oxygen-rich film assembly, an air compression assembly and a housing. The power unit is disposed on the support and comprises a pedaling and rotating mechanism and a load wheel in drive connection with the pedaling and rotating mechanism; the oxygen-rich film assembly is adapted to suck in and filter air to form oxygen-rich air; the air compression assembly comprises an integrated air compressor disposed on the support and connected with an output gas path of the oxygen-rich film assembly, the integrated air compressor is adapted to be activated in response to rotation of the pedaling and rotating mechanism to compress the oxygen-rich air to form an oxygen-rich air flow with a pressure difference for supply to the exerciser; and the housing is disposed on the support to cover the power unit, the oxygen-rich film assembly and the air compression assembly.

Wherein, the air compression assembly further comprises a first socketing piece, a supporting plate and a first elastic piece, wherein the first socketing piece is disposed on the integrated compressor; the supporting plate is disposed on the support and has a second socketing piece; the first elastic piece has one end thereof socketed to the first socketing piece and the other end socketed to the second socketing piece.

Wherein, the support comprises a base frame, a humidifying assembly, a supporting frame, a fixing rod, a supporting pipe and a horizontal connecting frame, wherein the base frame is adapted to support the supporting plate; the humidifying assembly is in fluid communication with the integrated air compressor and is adapted to receive the oxygen-rich air with a pressure difference that is inputted from the integrated air compressor and humidify the oxygen-rich air with a pressure difference; the supporting frame is disposed on the base frame to support the humidifying assembly; the fixing rod is disposed to be spaced apart from the supporting frame and is adapted to support and assemble the oxygen-rich film assembly; the supporting pipe is disposed to be spaced apart from the supporting frame; and the horizontal connecting frame has one end thereof connected with the supporting frame and the other end connected with the supporting pipe.

Wherein, the humidifying assembly comprises a baseplate, a fixing mount, a humidifying box, and a fastening frame, wherein the baseplate is disposed on the supporting frame; the fixing mount is disposed on the baseplate; a bottom portion of the humidifying box mates with the fixing mount and an end of the humidifying box has a third socketing piece; and the fastening frame is disposed to be apart from the fixing mount and movably connected with the baseplate or the housing to fasten the humidifying box into the fixing mount.

Wherein, the fastening frame comprises a fixing portion, a movable portion, a clasp portion, and a second elastic piece. The fixing portion is disposed on the baseplate or the housing; the movable portion is hinged to the fixing portion; one end of the clasp portion is connected with the movable portion and the other end of the clasp portion is adapted to clasp the humidifying box into the fixing mount; and one end of the second elastic piece is disposed on the movable portion and the other end of the second elastic piece is tightly pressed against the second socketing piece.

Wherein, the support further comprises a vertical rod, an inclined rod, a seat plate and a reinforcing plate, wherein the vertical rod is vertically disposed on the base frame; the inclined rod is obliquely disposed on a bottom portion of the base frame; the seat plate is disposed on the vertical rod and the inclined rod to bear the exerciser; and the reinforcing plate is disposed on the base frame and abutting against the vertical rod.

Wherein, the pedaling and rotating mechanism comprises a drive wheel, a crank and a pedal, wherein the drive wheel is in drive connection with the load wheel; the crank is hinged with the drive wheel at the supporting frame; and the pedal is connected with the crank and is adapted to provide a power for rotating the drive wheel so that the load wheel is driven to rotate.

Preferably, the pedal comprises a supporting plate, a protective cover, a movable buckle and a clasp strip, wherein the supporting plate is connected with an end of the crank and is adapted to support a foot of the exerciser; the protective cover has one end thereof connected to an end of the supporting plate and the other end connected to the other end of the supporting plate so as to clasp the foot of the exerciser to the supporting plate; the movable buckle is disposed at one side of the supporting plate, and has a bottom portion and a fastening portion movably connected with the bottom portion, with an opening portion being formed between the bottom portion and the fastening portion; and the clasp strip is connected with the protective cover and has a plurality of toothed racks spaced apart from each other, wherein the clasp strip is inserted through the opening portion and the fastening portion is pressed against the toothed racks so that the movable buckle is fastened by the clasp strip.

Wherein, the power unit further comprises a sensor unit and a control unit, wherein the sensor unit is disposed at one side of the drive wheel to detect the drive wheel and generate an activation signal when the drive wheel is rotating; and the control unit is disposed on the supporting frame and is configured to receive the activation signal to control activation or deactivation of the integrated air compressor.

Wherein, the power unit further comprises a supporting mount, two fixing plates, a magnet fixing mount and a magnet, wherein the supporting mount is disposed between the supporting pipe and the supporting frame and fixed to the base frame; the two fixing plates are disposed on the supporting mount and spaced apart from each other, with the load wheel being disposed between the two fixing plates; the magnet fixing mount is connected to end portions of the two fixing plates; and the magnet is disposed in the magnet fixing mount and is adapted to adjust rotation resistance of the load wheel under the control of the control unit.

The present disclosure has the following benefits: as compared with the prior art, a sensor unit, a control unit, a motor and an oxygen generator are provided in the automatic oxygen-generating fitness equipment of the present disclosure, and upon receiving an activation signal from the sensor, the control unit activates the motor to drive the oxygen generator to operate so that air favorable for the human body (air at a high oxygen concentration) can be supplied to the exercisers.

BRIEF DESCRIPTION OF THE DRAWINGS

To describe the technical solutions of embodiments of the present disclosure more clearly, the attached drawings necessary for description of the embodiments will be introduced briefly hereinbelow. Obviously, these attached drawings only illustrate some of the embodiments of the present disclosure, and those of ordinary skill in the art can further obtain other drawings according to these attached drawings without making inventive efforts. In the attached drawings.

DETAILED DESCRIPTION OF THE INVENTION

Hereinbelow, the present disclosure will be described in detail with reference to the attached drawings and embodiments thereof. It shall be appreciated that, the fitness equipment may be an exercise bicycle, a horizontal-type bicycle or any other fitness equipments capable of generating oxygen by means of their own mechanical energy. Hereinafter, only an exercise bicycle will be taken as an example for description.

Figure 1:
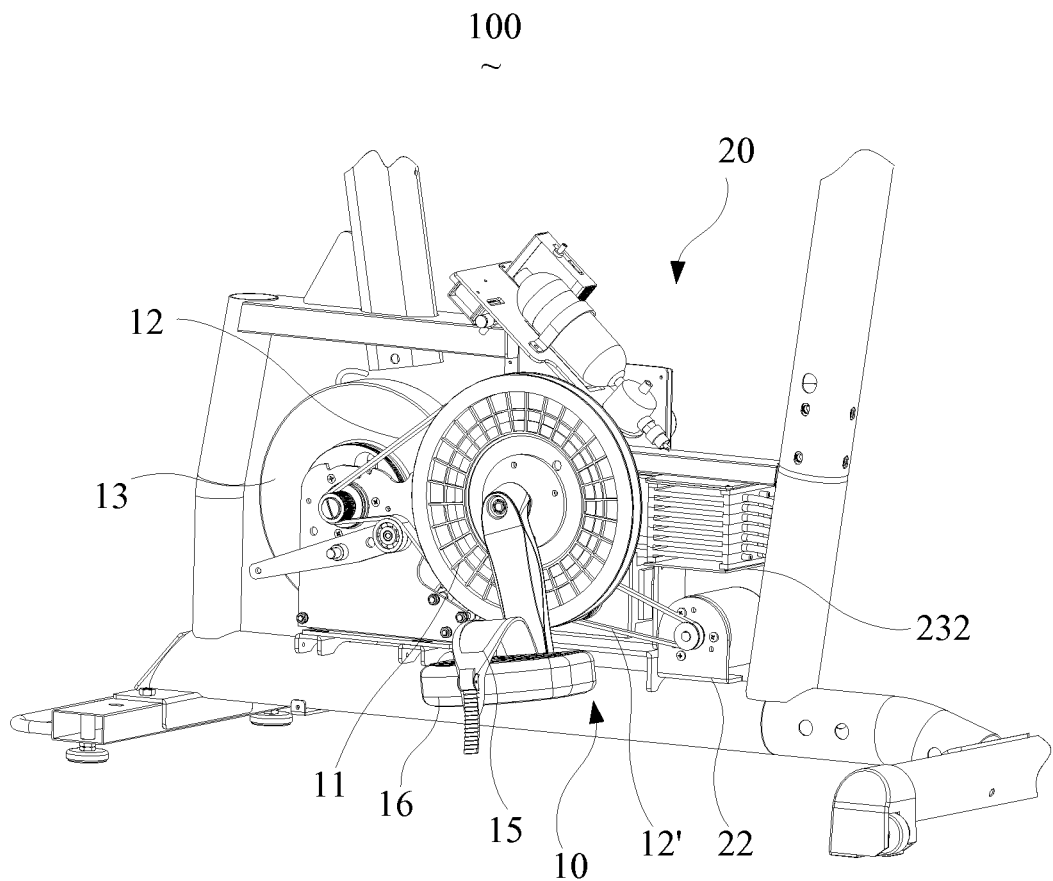
FIG. 1 is a front view showing internal structures of an automatic oxygen-generating fitness equipment according to an embodiment of the present disclosure.
Figure 2:
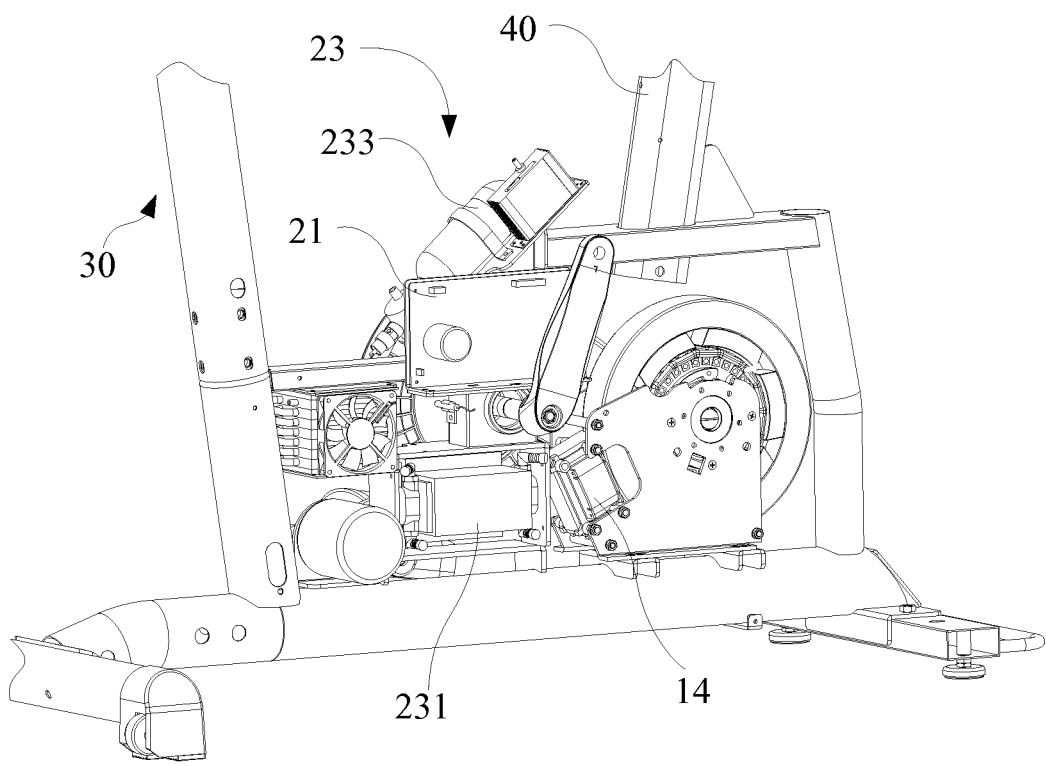
FIG. 2 is a back view showing internal structures of the automatic oxygen-generating fitness equipment shown in FIG. 1 according to the present disclosure.

Referring to FIG. 1 and FIG. 2 together, FIG. 1 is a front view showing internal structures of an automatic oxygen-generating fitness equipment according to the present disclosure, and FIG. 2 is a back view showing internal structures of the automatic oxygen-generating fitness equipment of the present disclosure shown in FIG. 1. The automatic oxygen-generating fitment equipment 100 of the present disclosure comprises a power unit 10, a sensor unit (not shown) and an oxygen-generating assembly 20.

The power unit 10 comprises a belt drive turnplate 11, a belt 12, a magnetic wheel 13, an electromagnet 14, a crank 15 and a pedal 16. The crank 15 is hinged to the belt drive turnplate 11, and the pedal 16 and the crank 15 are hinged together. During the exercise, the exerciser pedals the pedal 16 to rotate so that the belt drive turnplate 11 is driven by the crank 15 to rotate, and the rotation of the belt drive turnplate 11 drives the belt 12 to operate so that the magnetic wheel 13 is driven to rotate.

The sensor unit is adapted to detect the belt drive turnplate 11 and generate an activation signal when the belt drive turnplate 11 is rotating.

The oxygen-generating assembly 20 comprises a control unit 21, a motor 22, an oxygen generator 23, a second belt 12' and a power source (not shown). The control unit 21 is configured to receive the activation signal to activate the motor 22 so that the oxygen generator 23 is driven by the second belt 12' to operate. The power source supplies electric power to the motor 22 via the control unit 21, and the rotation resistance of the magnetic wheel 13 is adjusted by the electromagnet 14 under the control of the control unit 21. Specifically, the resistance force applied by the electromagnet 14 to the magnetic wheel 13 can be arbitrarily adjusted to achieve an exercise level desired by the exerciser.

The power source in this embodiment may be an external power source, and of course, may also be a power generator. Specifically, in the latter case, the kinetic energy generated by the exercising movement of the exerciser is finally transferred to the power generator as a driving source to drive the power generator to operate, thus converting the mechanic energy into electric power for supply to the motor 22. Further, the power unit 10 may also be provided with an energy storage device, e.g., a battery. The motor 22 is electrically connected to the power generator via the battery. In addition to supplying electric power to the motor 22 directly from the power generator so as to drive the motor 22 to operate, the electric power generated by the power generator can also be stored into the battery and later supplied to the motor 22 when necessary. As such, even after the power generator has stopped operation (e.g., when the exerciser is taking a rest), the motor 22 can still operate on the electric power already stored in the battery so that the oxygen generator 23 is powered to supply oxygen continuously. The exerciser can switch between these two operation modes depending on his or her specific need, and such a flexible design also represents a kind of human-based concept. Of course, the battery may also be used as a power source for any other devices if necessary so as to power these devices to operate.

The oxygen generator 23 comprises a vacuum pump 231, an oxygen-rich film 232, an oxygen bag 233 and medical-grade silicone tubes (not shown). The oxygen-rich film 232 and the oxygen bag 233 are connected to the vacuum pump 231 via the medical-grade silicone tubes respectively. Rotation of the motor 22 drives the vacuum pump 231 to generate an air stream so that air at a rated oxygen concentration is formed by the oxygen-rich film 232. The rated oxygen concentration ranges between 21% and 30%, and the air at the rated oxygen concentration from the oxygen-rich film 232 flows towards the oxygen bag 233 through the vacuum pump 231 at a flow rate of 10 L/min.

The oxygen generator 23 may, but is not limited to, take the form of the vacuum pump 231 and a carbon molecular sieve (not shown), and instead, any oxygen-generating device capable of being driven by the electric power or the mechanic energy can be applied in the automatic oxygen-generating fitness equipment 100 of the present disclosure.

The automatic oxygen-generating fitness equipment 100 of the present disclosure further comprises a switch (not shown). Under the control of the control unit 21, the switch is used to switch between an oxygen-generating mode and a non-oxygen-generating mode of the automatic oxygen-generating fitness equipment 100. In the oxygen-generating mode, the automatic oxygen-generating fitness equipment 100 can supply air favorable for the human body (i.e., air at a high oxygen concentration) to the exerciser, and in the non-oxygen-generating mode, the automatic oxygen-generating fitness equipment 100 only has the fitness function.

The automatic oxygen-generating fitness equipment 100 further comprises an armrest (not shown), a frame 30 and a seat cushion frame 40. The power unit 10 and the oxygen-generating assembly 20 are disposed in the frame 30, the seat cushion frame 40 and the armrest are connected to the frame 30 respectively, and the oxygen bag 233 is disposed between the seat cushion frame 40 and the armrest to supply air at the rated oxygen concentration to the exerciser. Specifically, the oxygen bag 233 is disposed on the frame 30, and an angle is included between the oxygen bag 233 and a direction in which the user tilts during the exercise so that the air at the rated oxygen concentration from an air outlet of the oxygen bag 233 flows towards the exerciser's nose at a flow rate of 10 L/min. Of course, a wearable mask may be additionally provided so that the air at the rated oxygen concentration from the oxygen bag 233 is transferred via a conduit to the mask directly to supply oxygen to the exerciser. With the individual parts of the automatic oxygen-generating fitness equipment 100 of the present disclosure and connection relationships therebetween having been described briefly above, the operation process thereof will be further described below.

During the exercise, the pedal 16 is pedaled to rotate by the exerciser and the belt drive turnplate 11 is driven to rotate by the crank 15, and the rotation of the belt drive turnplate 11 drives the belt 12 to operate so that the magnetic wheel 13 is driven to rotate. The rotation resistance of the magnetic wheel 13 is adjusted by the electromagnet 14 under the control of the control unit 21 to adjust the exercise level of the exerciser. Meanwhile, the belt 12 rotates and thus causes the sensor to generate a sensing signal, then via the control unit 21, the sensor unit automatically activates the motor 22 to operate, and the power source supplies power to the motor 21 via the control unit 21. Finally, the vacuum pump 231 is driven by the second belt 12' to generate an air stream from the oxygen-rich film 232. Then, after the air stream is filtered by the carbon molecular sieve in the oxygen-rich film 232, the oxygen concentration of the air is increased from 21% to 21~30%. The air at the increased oxygen concentration flows through the oxygen bag 233 to reach a flow rate of 10 L/min and is then transferred to the exerciser to meet the oxygen concentration demand of the human body. In this way, oxygen can be generated during the exercise to provide a sufficient amount of oxygen needed by the human body.

Because the sensor unit, the control unit 21, the motor 22 and the oxygen generator 23 are disposed in the automatic oxygen-generating fitness equipment 100 of the present disclosure, an activation signal can be sent from the sensor to the control unit 21 which then activates the motor 22 to operate so that the oxygen generator 23 operates to supply oxygen to the exerciser.

Figure 3:
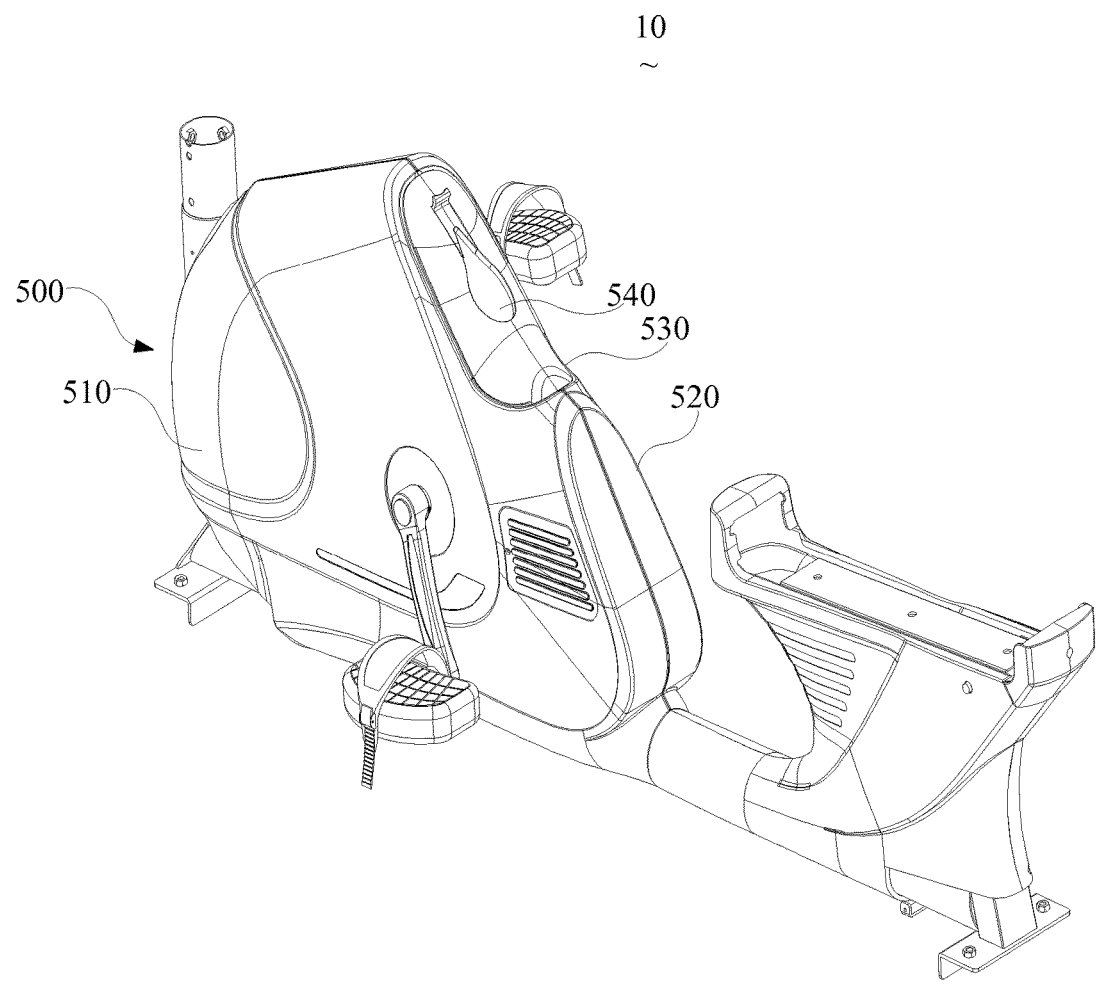
FIG. 3 is a perspective view showing partial structures of a fitness equipment according to the present disclosure.
Figure 4:
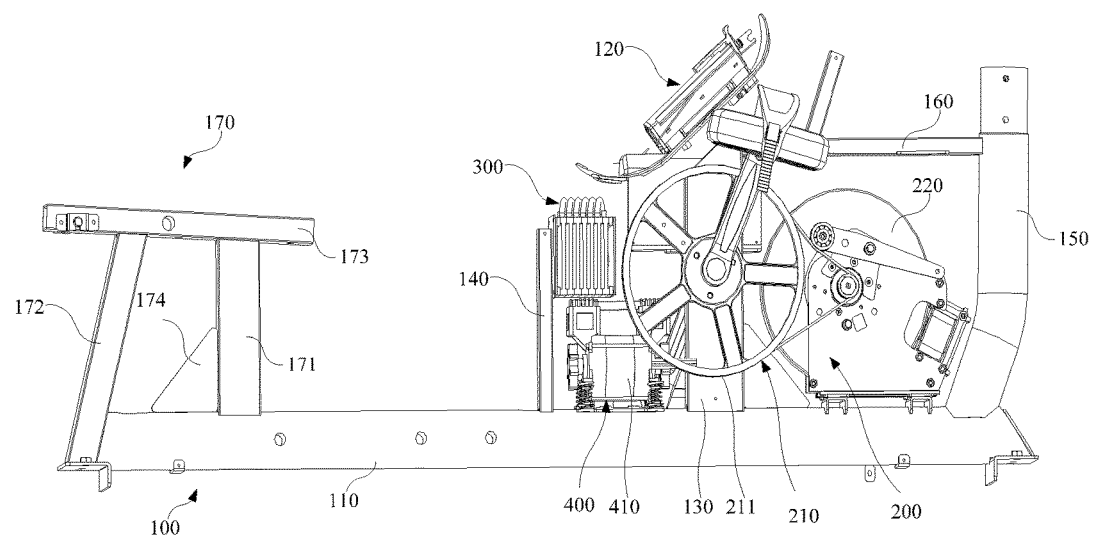
FIG. 4 is a perspective view showing internal structures of the fitness equipment shown in FIG. 3.

Referring to FIG. 3, there is shown a perspective view showing partial structures of the fitness equipment of the present disclosure. FIG. 4 is a perspective view showing internal structures of the fitness equipment shown in FIG. 3. The present disclosure further provides a fitness equipment 10, which comprises a support 100, a power unit 200, an oxygen-rich film assembly 300, an air compression assembly 400 and a housing 500. The power unit 200 is disposed on the support 100. The power unit 200 comprises a pedaling and rotating mechanism 210 and a load wheel 220 in drive connection with the pedaling and rotating mechanism 210. The load wheel 220 may be a magnetic wheel, or some other wheel for which the resistance can be manually controlled by means of a brake pad. The oxygen-rich film assembly 300 is adapted to suck in and filter the air to form oxygen-rich air. The air compression assembly 400 comprises an integrated air compressor 410 which is disposed on the support and connected with an output gas path of the oxygen-rich film assembly 300. The integrated air compressor 410 is activated in response to rotation of the pedaling and rotating mechanism. Because the integrated air compressor 410 continuously compresses the oxygen-rich air in a cavity thereof and outputs the compressed oxygen-rich air into a humidifying box 123 (to be described later), a pressure difference is formed across the oxygen-rich air within the integrated air compressor 410 so that the oxygen-rich air from the output path of the oxygen-rich film assembly 300 is extracted continuously to make the air pressure at the input end of the oxygen-rich film assembly 300 higher than the oxygen-rich air pressure at the output end. Thereby, the oxygen-rich film assembly 300 continuously sucks in and filters the air to form oxygen-rich air for supply to the integrated air compressor 410, and the integrated air compressor 410 compresses the extracted oxygen-rich air to produce the oxygen-rich air with a pressure difference for supply to the exerciser or an air collection tank. This process continues until a signal indicating that the load wheel 220 has stopped is received. The integrated air compressor 410 of the present disclosure may be an oilless air compressor. The oxygen-rich film assembly 300 may be a part for filtering the air and concentrating the oxygen such as an oxygen-rich film or a molecular sieve.

The housing 500 of the present disclosure is disposed on the support 100 to cover the power unit, the oxygen-rich film assembly 300 and the air compression assembly 400. As shown in FIG. 3, the housing 500 comprises a left enclosure 510, a right enclosure 520 and a cover plate 530. The left enclosure 510 and the right enclosure 520 cooperate with each other and joined together to form an opening, and the cover plate 530 covers the opening. The cover plate 530 has a through-hole 540, which may be in an elliptical shape, a circular shape, or a bowling pin shape.

The support 100 of the present disclosure comprises a base frame 110, a humidifying assembly 120, a supporting frame 130, a fixing rod 140, a supporting pipe 150 and a horizontal connecting frame 160. The base frame 110 is in a tubular form, but may also be in other forms such as a square form. The humidifying assembly 120 is in fluid communication with the integrated air compressor 410, and is adapted to receive the oxygen-rich air having a pressure difference that is inputted from the integrated air compressor 410 and humidify the oxygen-rich air. The supporting frame 130 is disposed on the base frame 110 to support the humidifying assembly 120. The fixing rod 140 is disposed to be spaced apart from the supporting frame 130 and is adapted to support and assemble the oxygen-rich film assembly 300. The supporting pipe 150 is disposed to be spaced apart from the supporting frame 130. The horizontal connecting frame 160 has one end thereof connected to the supporting frame 130 and the other end connected to the supporting pipe 150.

Figure 5:
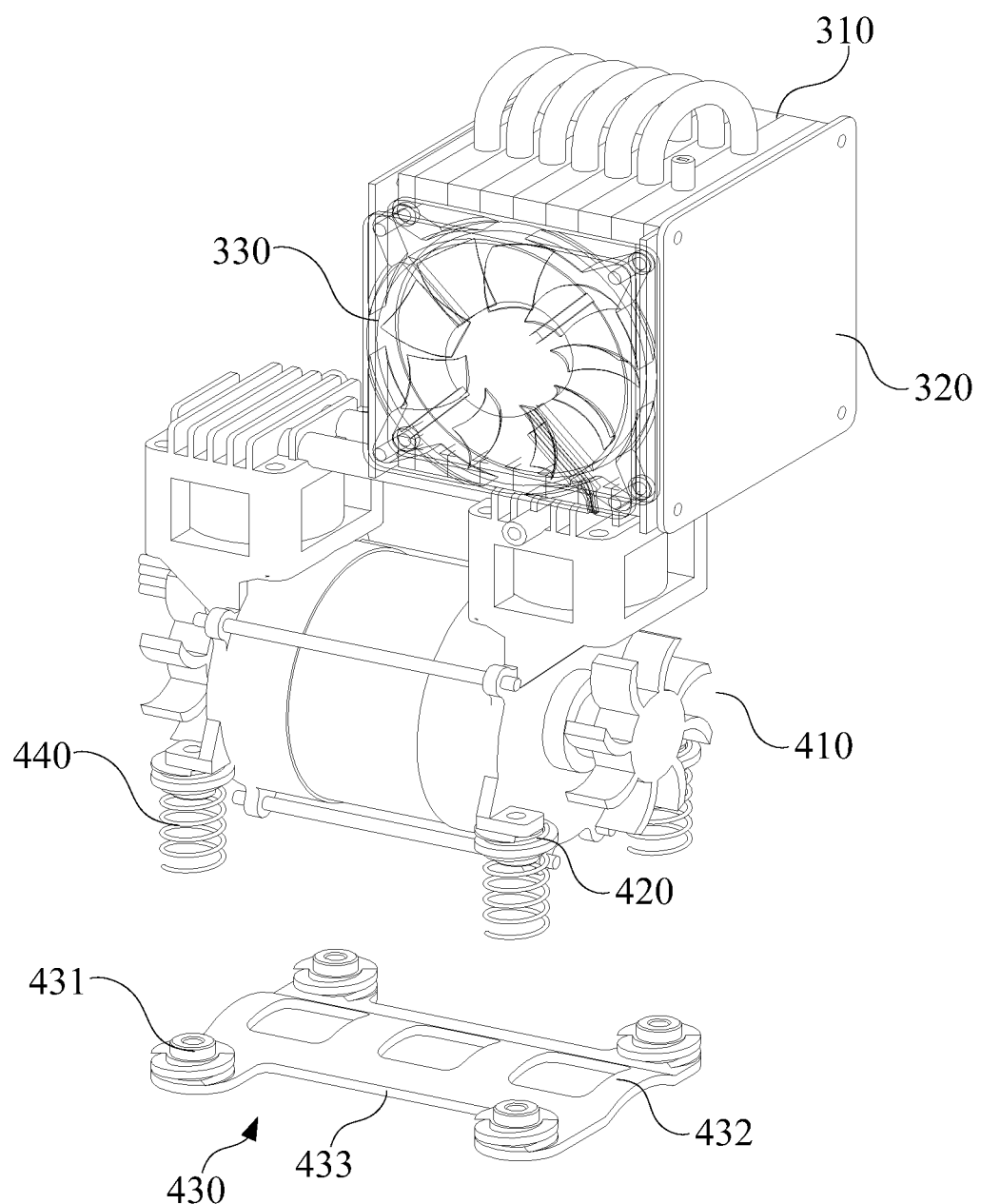
FIG. 5 is a perspective view showing the connection between an air compression assembly and an oxygen-rich film assembly of the fitness equipment shown in FIG. 4.

Referring to FIG. 5 together, there is shown a perspective view showing the connection between the air compression assembly and the oxygen-rich film assembly of the fitness equipment shown in FIG. 4. The air compression assembly 400 of the present disclosure further comprises a first socketing piece 420, a supporting plate 430 and a first elastic piece 440. The supporting plate 430 is disposed on the base frame 110, and has a second socketing piece 431. The supporting plate 430 has, in the middle thereof, an arc-shaped portion 432 that matches with the base frame 110, and horizontal plates 433 are formed at two sides of the arc-shaped portion 432 to support the integrated air compressor 410 in a horizontal state. The first elastic piece 440 has one end thereof socketed around the first socketing piece 420 and the other end socketed around the second socketing piece 431. Specifically, the first socketing piece 420 and the second socketing piece 431 may be in a columnar form, and of course, may also be in the form of a recess in which case the first elastic piece 440 is inserted into the recesses. The first elastic piece 440 may be a spring, or an elastic column made of silicone, rubber or some other elastic material. The oxygen-rich film assembly 300 comprises an oxygen-rich film 310, a connecting plate 320 and a fan 330. The oxygen-rich film 310 is fixed to the fixing rod 140 by means of the connecting plate 320. The oxygen-rich film 310 is disposed on the integrated air compressor 410, and by virtue of the supporting effect of the integrated air compressor 410, the pressing force applied by the oxygen-rich film 310 to the fixing rod 140 can be reduced. The fan 330 is disposed at an air inlet of the oxygen-rich film 310 to accelerate the flow of air so that the air can be sucked in from the atmosphere more quickly by the oxygen-rich film 310.

As shown in FIG. 4, the support 100 further comprises a seat fixing frame 170 disposed on the base frame 110. The seat fixing frame 170 comprises a vertical rod 171, an inclined rod 172, a seat plate 173 and a reinforcing plate 174. The vertical rod 171 is vertically disposed on the base frame 110, the inclined rod 172 is obliquely disposed on a bottom portion of the base frame 110, the vertical rod 171 and the inclined rod 172 are used to support the seat plate 171, and the reinforcing plate 174 is disposed on the base frame 110 and abuts against the vertical rod 171.

Figure 6:
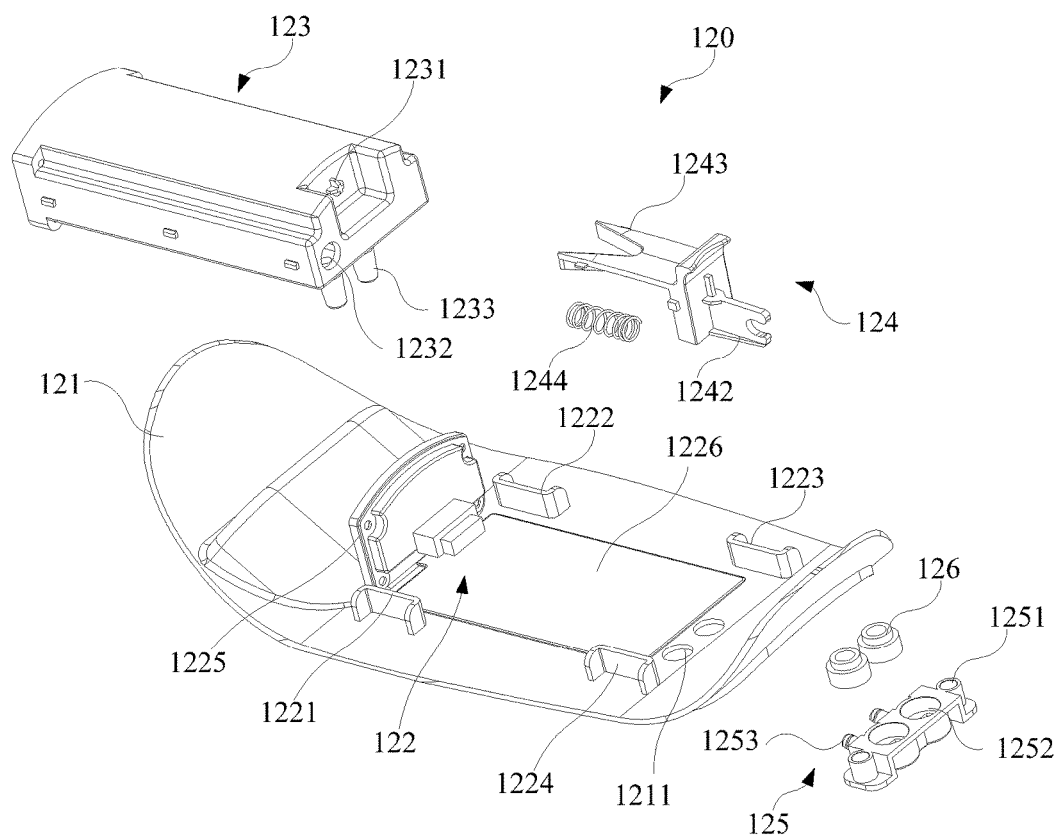
FIG. 6 is an exploded view of a humidifying assembly of the fitness equipment shown in FIG. 4.

Referring to FIG. 6, there is shown an exploded view of the humidifying assembly of the fitness equipment shown in FIG. 4. The humidifying assembly 120 comprises a baseplate 121, a fixing mount 122, a humidifying box 123, a fastening frame 124, a socketing mount 125 and a pressing bushing 126. The baseplate 121 matches with the housing 500 and is disposed on the supporting frame 130. The baseplate 121 has a through hole 1211 and is formed with a boss (not shown) at the back thereof, and the fixing mount 122 is disposed on the baseplate 121 and is opposite to the boss. A bottom portion of the humidifying box 123 mates with the fixing mount 122. Specifically, as shown in FIG. 4, the fixing mount 122 comprises a first fixing block 1221, a second fixing block 1222, a third fixing block 1223, a fourth fixing block 1224 and a stopper 1225. The first fixing block 1221, the second fixing block 1222, the third fixing block 1223 and the fourth fixing block 1224 are arrayed in a square form on the baseplate 121 to enclose a fixing cavity 1226 that matches with the humidifying box 123, and the stopper 1225 is disposed between the first fixing block 1221 and the second fixing block 1222 to stop the humidifying box 123 from sliding out of the fixing cavity 1226. At an end of the humidifying box 123, a third socketing piece 1231, a water inlet 1232 and a vent column 1233 are disposed. The socketing mount 125 has a connecting portion 1251, a socketing opening 1252 and an air inlet 1253. The connecting portion 1251 matches with the boss of the baseplate 121. Specifically, the connecting portion 1251 has a socket into which the boss is to be inserted, and the pressing bushing 126 matches with the vent column 1233 of the humidifying box 123 and is disposed in the socketing opening 1252. Specifically, the vent column 1233 of the humidifying box 123 passes through the through hole 1211 of the baseplate 121 and mates with the pressing bushing 126 disposed in the socketing opening 1252, and the air inlet 1253 is in fluid communication with the integrated air compressor 410 so that the oxygen-rich air having the pressure difference flows from the integrated air compressor 410 through the air inlet 1253 and the vent column 1233 into the humidifying box 123. The oxygen-rich air having the pressure difference that flows into the humidifying box 123 is humidified by the humidifying box 123 and filtered for output to the exerciser or an air collection tank. The fastening frame 124 is disposed to be spaced apart from the fixing mount 122 and is movably connected to the baseplate 121 or the housing 500 to fasten the humidifying box 123 into the fixing mount 122. The fastening frame 124 comprises a fixing portion (not shown), a movable portion 1242, a clasp portion 1243 and a second elastic piece 1244. The fixing portion is disposed on the baseplate 121, and of course, the fixing portion may also be disposed on the housing 500. The movable portion 1242 is hinged to the fixing portion. One end of the clasp portion 1243 is connected to the movable portion 1242 and the other end is adapted to clasp the humidifying box 123 into the fixing mount 122. One end of the clasp portion 1243 is in a U shape, and the U-shaped end matches with the through hole 540 of the cover 530. The second elastic piece 1244 has one end disposed on the movable portion 1242 and the other end tightly pressed against the third socketing piece 1231. The second elastic piece 1244 may be a spring, or an elastic column made of silicone, rubber or some other elastic material.

The pedaling and rotating mechanism 210 comprises a drive wheel 211, a crank 212 and a pedal 213. The drive wheel 211 is in drive connection with the load wheel 220. The drive connection may be accomplished by a belt, a chain or the like, and the drive wheel 211 may be a belt drive turnplate. The crank 212 is hinged with the drive wheel 211 at the supporting frame 130. The pedal 213 is connected with the crank 212, and is adapted to provide power for rotating the drive wheel 211 so that the load wheel 220 is driven to rotate.

Figure 7:
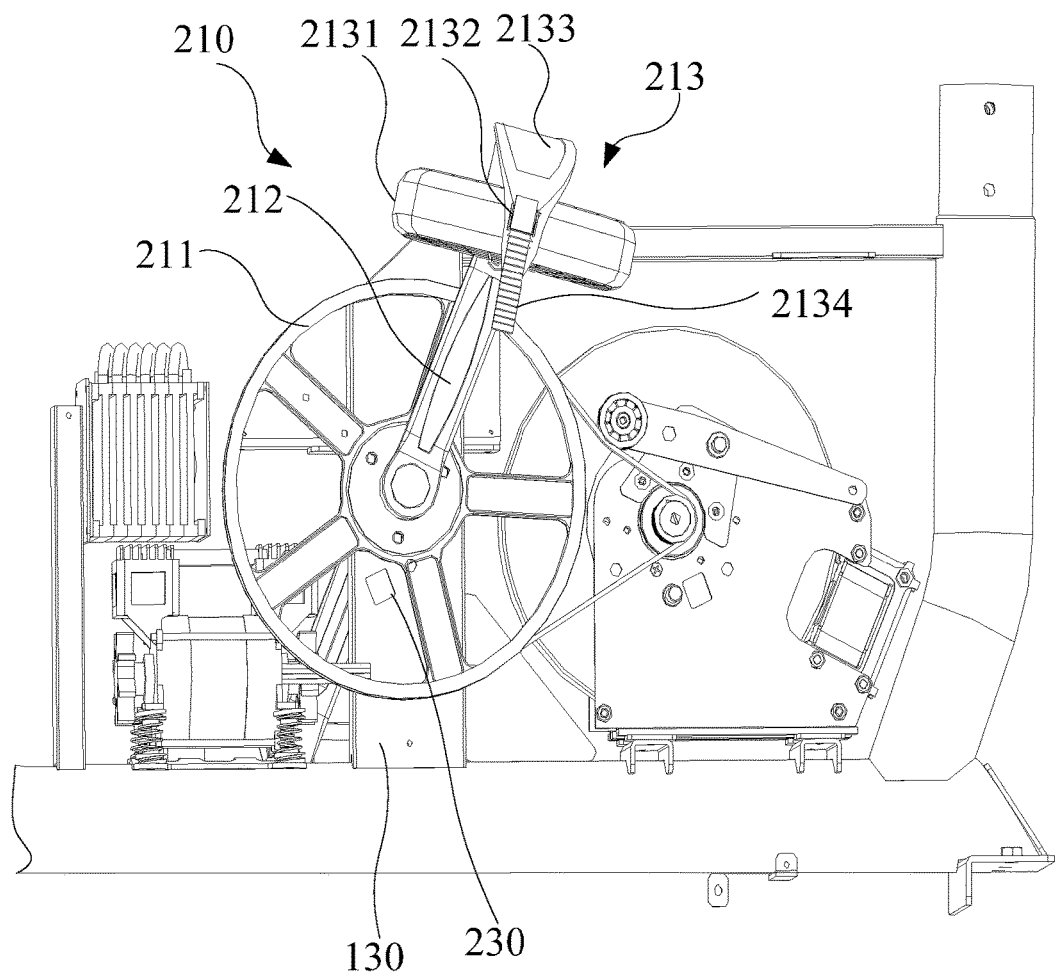
FIG. 7 is a perspective view showing a side of a power unit of the fitness equipment shown in FIG. 4.

Referring to FIG. 7 together, there is shown a perspective view showing a side of the power unit of the fitness equipment shown in FIG. 4. The pedal 213 comprises a supporting plate 2131, a protective cover 2132, a movable buckle 2133 and a clasp strip 2134. The supporting plate 2131 is connected with an end of the crank 212, and is adapted to support a foot of the exerciser. The protective cover 2132 has one end thereof connected to an end of the supporting plate 2131 and the other end connected to the other end of the supporting plate 2131 so as to clasp the foot of the exerciser to the supporting plate 2131. The movable buckle 2133 is disposed at one side of the supporting plate 2131, and has a bottom portion and a fastening portion movably connected with the bottom portion, with an opening portion being formed between the bottom portion and the fastening portion. The clasp strip 2134 is connected with the protective cover 2132, and has a plurality of toothed racks spaced apart from each other. The clasp strip 2134 is inserted through the opening portion and the fastening portion is pressed against the toothed racks so that the movable buckle is fastened by the clasp strip.

Figure 8:
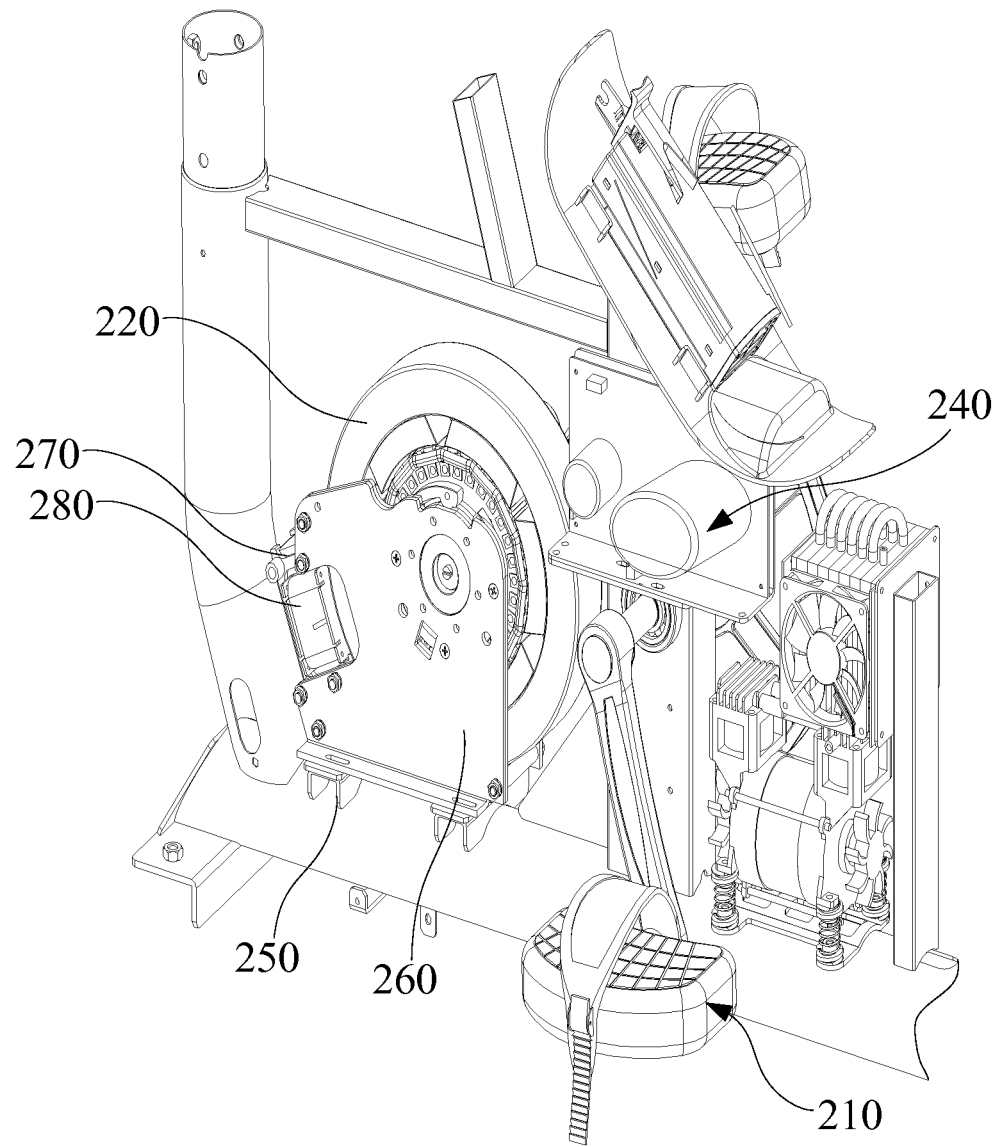
FIG. 8 is a perspective view showing the other side of the power unit shown in FIG. 7.

Referring to FIG. 8 together, there is shown a perspective view showing the other side of the pedal of the fitness equipment shown in FIG. 7. The power unit 200 of the present disclosure further comprises a sensor unit 230, a control unit 240, a supporting mount 250, two fixing plates 260, a magnet fixing mount 270 and a magnet 280. The sensor unit 230 is disposed at one side of the drive wheel 211 to detect the load wheel 220 and generate an activation signal when the load wheel 220 is rotating and generate a deactivation signal when the load wheel 220 stops rotating. The sensor unit 230 of the present disclosure may be disposed on the supporting frame 130 or on the housing 500. The control unit 240 is disposed on the supporting frame 130, and is configured to receive the activation signal or the deactivation signal to control activation or deactivation of the integrated air compressor 410. It is worth noting that, the activation signal or deactivation signal received by the control unit 240 is not limited to an activation signal or deactivation signal generated by detecting whether the drive wheel 211 is rotating, but may also be an activation signal or deactivation signal generated by the sensor through detecting whether the load wheel 220 is rotating or not. The supporting mount 250 is disposed between the supporting pipe 150 and the supporting frame 130 and fixed to the base frame 110. The supporting mount 250 may be one flat plate, or may be composed of four supporting blocks arrayed in a square form on the base frame 110. The two fixing plates 260 are disposed on the supporting mount 250 and spaced apart from each other. The load wheel 220 is disposed between the two fixing plates 260. The magnet fixing mount 270 is connected to end portions of the two fixing plates 260. The magnet 280 is disposed in the magnet fixing mount 270, and is adapted to adjust rotation resistance of the load wheel 220 under the control of the control unit 240.

The power unit 200 of the present disclosure further comprises a power source (not shown), which supplies electric power to the integrated air compressor 410 according to a control signal from the control unit 240. The power source may be an external power source, and of course, may also be a power generator. In the latter case, the kinetic energy generated by the exercising movement of the exerciser is finally transferred to the power generator as a driving source to drive the power generator to operate, thus converting the mechanic energy into electric power for powering the integrated air compressor 410. Further, the power unit 20 may also be provided with an energy storage device, e.g., a battery. The integrated air compressor 410 is connected to the power generator via the battery. In addition to supplying electric power to the integrated air compressor 410 directly from the power generator so as to drive the integrated air compressor 410 to operate, the electric power generated by the power generator can also be stored into the battery and later supplied to the integrated air compressor 410 or to other electricity-consuming parts at specific times when necessary. As such, even after the power generator has stopped operation (e.g., when the exerciser is taking a rest), the integrated air compressor 410 or other parts operating on electrical power can still operate on the electric power already stored in the battery.

Because the fitness equipment of the present disclosure is provided with an integrated air compressor, the complex and fragile structure of the conventional fitness equipment in which a motor is needed to drive, via a belt, the vacuum pump to compress the air is eliminated. Thereby, the fitness equipment of the present disclosure is simple and compact in structure and is convenient to use, and this reduces the volume of the equipment and lowers the material cost.

What described above are only the embodiments of the present disclosure, but are not intended to limit the scope of the present disclosure. Any equivalent structures or equivalent process flow modifications that are made according to the specification and the attached drawings of the present disclosure, or any direct or indirect applications of the present disclosure in other related technical fields shall all be covered within the scope of the present disclosure.

What is claimed is:

1. An automatic oxygen-generating fitness equipment, comprising:
   a power unit, comprising a belt drive turnplate, a belt and a magnetic wheel, wherein rotation of the belt drive turnplate drives the belt to operate so that the magnetic wheel is driven to rotate;
   a sensor unit configured to detect the belt drive turnplate and generate an activation signal when the belt drive turnplate is rotating;
   an oxygen-generating assembly, comprising a control unit, a motor and an oxygen generator, wherein the control unit is configured to receive the activation signal so that the motor is activated to drive the oxygen generator to operate.

2. The automatic oxygen-generating fitness equipment of claim 1, wherein the oxygen generator comprises a vacuum pump and an oxygen-rich film, and rotation of the motor drives the vacuum pump to generate an air stream so that air at a rated oxygen concentration is formed by the oxygen-rich film.

3. The automatic oxygen-generating fitness equipment of claim 2, wherein the oxygen generator further comprises an oxygen bag, and the air at the rated oxygen concentration flows to the oxygen bag via the vacuum pump.

4. The automatic oxygen-generating fitness equipment of claim 3, wherein the oxygen bag forms the air at the rated oxygen concentration into an air flow of 10 L/min to supply to an exerciser.

5. The automatic oxygen-generating fitness equipment of claim 4, wherein the oxygen generator further comprises medical-grade silicone tubes, and the oxygen-rich film and the oxygen bag are connected to the vacuum pump via the medical-grade silicone tubes respectively.

6. The automatic oxygen-generating fitness equipment of claim 5, wherein the rated oxygen concentration is 21%-30%.

7. The automatic oxygen-generating fitness equipment of claim 4, further comprising:
   an armrest;
   a frame, wherein the power unit and the oxygen-generating assembly are disposed in the frame; and
   a seat cushion support, where the seat cushion support and the armrest are connected with the frame respectively, and the oxygen bag is disposed between the seat cushion support and the armrest to provide the exerciser with the air at the rated oxygen concentration.

8. The automatic oxygen-generating fitness equipment of claim 1, wherein the power unit further comprises an electromagnet which is adapted to adjust rotation resistance of the magnetic wheel under the control of the control unit.

9. The automatic oxygen-generating fitness equipment of claim 1, wherein the oxygen-generating assembly further comprises an external electric power source which supplies electric power to the motor via the control unit.

10. The automatic oxygen-generating fitness equipment of claim 1, wherein the power unit further comprises:
   a crank hinged to the belt drive turnplate; and
   a pedal hinged to the crank, being adapted to drive the belt drive turnplate to rotate via the crank.

11. A fitness equipment, comprising:
   a support;
   a power unit disposed on the support, the power unit comprising a pedaling and rotating mechanism and a load wheel in drive connection with the pedaling and rotating mechanism;
   an oxygen-rich film assembly, being adapted to suck in and filter air to form oxygen-rich air;
   an air compression assembly, comprising an integrated air compressor disposed on the support and connected with an output gas path of the oxygen-rich film assembly, the integrated air compressor being adapted to be activated in response to rotation of the pedaling and rotating mechanism to compress the oxygen-rich air to form an oxygen-rich air flow with a pressure difference for supply to the exerciser; and
   a housing disposed on the support to cover the power unit, the oxygen-rich film assembly and the air compression assembly;
   wherein the air compression assembly further comprises:
      a first socketing piece disposed on the integrated compressor;
      a supporting plate disposed on the support and having a second socketing piece; and
      a first elastic piece, having one end thereof socketed to the first socketing piece and the other end socketed to the second socketing piece;
   the support comprises:
      a base frame, being adapted to support the supporting plate;
      a humidifying assembly in fluid communication with the integrated air compressor, being adapted to receive the oxygen-rich air with a pressure difference that is inputted from the integrated air compressor and humidify the oxygen-rich air with a pressure difference;
      a supporting frame disposed on the base frame to support the humidifying assembly;
      a fixing rod disposed to be spaced apart from the supporting frame, being adapted to support and assemble the oxygen-rich film assembly;
      a supporting pipe disposed to be spaced apart from the supporting frame; and
      a horizontal connecting frame, having one end thereof connected with the supporting frame and the other end connected with the supporting pipe;
   the humidifying assembly comprises:
      a baseplate disposed on the supporting frame;
      a fixing mount disposed on the baseplate;
      a humidifying box, a bottom portion of which mates with the fixing mount and an end of the humidifying box having a third socketing piece; and
      a fastening frame disposed to be apart from the fixing mount and movably connected with the baseplate or the housing to fasten the humidifying box into the fixing mount.

12. The fitness equipment of claim 11, wherein the fastening frame comprises:
   a fixing portion disposed on the baseplate or the housing;
   a movable portion hinged to the fixing portion;
   a clasp portion, one end of which is connected with the movable portion and the other end is adapted to clasp the humidifying box into the fixing mount; and
   a second elastic piece, one end of which is disposed on the movable portion and the other end is tightly pressed against the second socketing piece.

13. The fitness equipment of claim 11, wherein the support further comprises:
   a vertical rod vertically disposed on the base frame;

an inclined rod obliquely disposed on a bottom portion of the base frame;
a seat plate disposed on the vertical rod and the inclined rod to bear the exerciser; and
a reinforcing plate disposed on the base frame and abutting against the vertical rod.

14. The fitness equipment of claim 13, wherein the pedaling and rotating mechanism comprises:
a drive wheel in drive connection with the load wheel;
a crank hinged with the drive wheel at the supporting frame; and
a pedal connected with the crank, being adapted to provide power for rotating the drive wheel so that the load wheel is driven to rotate.

15. The fitness equipment of claim 14, wherein the pedal comprises:
a supporting plate connected with an end of the crank, being adapted to support a foot of the exerciser;
a protective cover, having one end thereof connected to an end of the supporting plate and the other end connected to the other end of the supporting plate so as to clasp the foot of the exerciser to the supporting plate;
a movable buckle disposed at one side of the supporting plate, having a bottom portion and a fastening portion movably connected with the bottom portion, with an opening portion being formed between the bottom portion and the fastening portion; and
a clasp strip connected with the protective cover, having a plurality of toothed racks spaced apart from each other, wherein the clasp strip is inserted through the opening portion and the fastening portion is pressed against the toothed racks so that the movable buckle is fastened by the clasp strip.

16. The fitness equipment of claim 14, wherein the power unit further comprises:
a sensor unit disposed at one side of the drive wheel to detect the drive wheel and generate an activation signal when the drive wheel is rotating; and
a control unit disposed on the supporting frame, being configured to receive the activation signal to control activation or deactivation of the integrated air compressor.

17. The fitness equipment of claim 16, wherein the power unit further comprises:
a supporting mount disposed between the supporting pipe and the supporting frame and fixed to the base frame;
two fixing plates disposed on the supporting mount and spaced apart from each other, with the load wheel being disposed between the two fixing plates;
a magnet fixing mount connected to end portions of the two fixing plates; and
a magnet disposed in the magnet fixing mount, being adapted to adjust rotation resistance of the load wheel under the control of the control unit.

18. A fitness equipment, comprising:
a support;
a power unit disposed on the support, the power unit comprising a pedaling and rotating mechanism and a load wheel in drive connection with the pedaling and rotating mechanism;
an oxygen-rich film assembly, being adapted to suck in and filter air to form oxygen-rich air;
an air compression assembly, comprising an integrated air compressor disposed on the support and connected with an output gas path of the oxygen-rich film assembly, the integrated air compressor being adapted to be activated in response to rotation of the pedaling and rotating mechanism to compress the oxygen-rich air to form an oxygen-rich air flow with a pressure difference for supply to the exerciser; and
a housing disposed on the support to cover the power unit, the oxygen-rich film assembly and the air compression assembly;
wherein the air compression assembly further comprises:
a first socketing piece disposed on the integrated compressor;
a supporting plate disposed on the support and having a second socketing piece; and
a first elastic piece, having one end thereof socketed to the first socketing piece and the other end socketed to the second socketing piece;
the support comprises:
a base frame, being adapted to support the supporting plate;
a humidifying assembly in fluid communication with the integrated air compressor, being adapted to receive the oxygen-rich air with a pressure difference that is inputted from the integrated air compressor and humidify the oxygen-rich air with a pressure difference;
a supporting frame disposed on the base frame to support the humidifying assembly;
a fixing rod disposed to be spaced apart from the supporting frame, being adapted to support and assemble the oxygen-rich film assembly;
a supporting pipe disposed to be spaced apart from the supporting frame; and
a horizontal connecting frame, having one end thereof connected with the supporting frame and the other end connected with the supporting pipe;
the support further comprises:
a vertical rod vertically disposed on the base frame;
an inclined rod obliquely disposed on a bottom portion of the base frame;
a seat plate disposed on the vertical rod and the inclined rod to bear the exerciser; and
a reinforcing plate disposed on the base frame and abutting against the vertical rod;
the pedaling and rotating mechanism comprises:
a drive wheel in drive connection with the load wheel;
a crank hinged with the drive wheel to the supporting frame;
a pedal connected with the crank, being adapted to provide a power for rotating the drive wheel so that the load wheel is driven to rotate;
the power unit further comprises:
a sensor unit disposed at one side of the drive wheel to detect the drive wheel and generate an activation signal when the drive wheel is rotating; and
a control unit disposed on the supporting frame, being configured to receive the activation signal to control activation or deactivation of the integrated air compressor.

19. The fitness equipment of claim 18, wherein the power unit further comprises:
a supporting mount disposed between the supporting pipe and the supporting frame and fixed to the base frame;
two fixing plates disposed on the supporting mount and spaced apart from each other, with the load wheel being disposed between the two fixing plates;
a magnet fixing mount connected to end portions of the two fixing plates; and a magnet disposed in the magnet fixing mount, being adapted to adjust rotation resistance of the load wheel under the control of the control unit.

\* \* \* \* \*